(12) United States Patent
Battrell et al.

(10) Patent No.: US 8,835,146 B2
(45) Date of Patent: Sep. 16, 2014

(54) REHYDRATABLE MATRICES FOR DRY STORAGE OF TAQ POLYMERASE IN A MICROFLUIDIC DEVICE

(75) Inventors: C. Frederick Battrell, Redmond, WA (US); Denise Maxine Hoekstra, Monroe, WA (US); Joan Haab, Seattle, WA (US); John R. Williford, Sammamish, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 13/323,675

(22) Filed: Dec. 12, 2011

(65) Prior Publication Data

US 2012/0142070 A1 Jun. 7, 2012

Related U.S. Application Data

(63) Continuation of application No. PCT/US2010/038140, filed on Jun. 10, 2010.

(60) Provisional application No. 61/186,441, filed on Jun. 12, 2009.

(51) Int. Cl.
*C12N 9/96* (2006.01)
*C12Q 1/70* (2006.01)
*C12N 9/12* (2006.01)
*B01L 3/00* (2006.01)

(52) U.S. Cl.
CPC ........... *C12N 9/96* (2013.01); *B01L 2200/16* (2013.01); *C12N 9/1252* (2013.01); *B01L 3/5027* (2013.01)
USPC ......................................... 435/188; 435/6.12

(58) Field of Classification Search
None
See application file for complete search history.

(56) References Cited

U.S. PATENT DOCUMENTS

| | | | |
|---|---|---|---|
| 4,206,200 A | 6/1980 | Guthöhrlein et al. | |
| 4,457,916 A | 7/1984 | Hayashi et al. | |
| 4,762,857 A | 8/1988 | Bollin, Jr. et al. | |
| 4,891,319 A | 1/1990 | Roser | |
| 5,098,893 A | 3/1992 | Franks et al. | |
| 5,200,399 A | 4/1993 | Wettlaufer et al. | |
| 5,234,809 A | 8/1993 | Boom et al. | |
| 5,565,318 A | 10/1996 | Walker et al. | |
| 5,593,824 A | 1/1997 | Treml et al. | |
| 5,763,157 A * | 6/1998 | Treml et al. | 435/4 |

(Continued)

FOREIGN PATENT DOCUMENTS

| | | |
|---|---|---|
| EP | 1803825 A1 | 7/2007 |
| GB | 2009198 A | 10/1978 |

(Continued)

OTHER PUBLICATIONS

NewProducts (Science, 2006, vol. 314, p. 323).*

(Continued)

*Primary Examiner* — Alexander Kim
(74) *Attorney, Agent, or Firm* — Seed IP Law Group, PLLC

(57) ABSTRACT

Formulations for dry storage of PCR reagents are described. These formulations find use in manufacture of self-contained microfluidic card devices for PCR clinical testing in which the reagents are reconstituted at the point of testing. In these cards, TAQ polymerase is stored "on-board" in vitrified dry form without lyophilization or freezing, and is reconstituted by either the sample or a sample eluate during the assay.

20 Claims, 4 Drawing Sheets

(56) References Cited

U.S. PATENT DOCUMENTS

| | | |
|---|---|---|
| 5,861,251 A | 1/1999 | Park et al. |
| 5,955,448 A | 9/1999 | Colaco et al. |
| 6,071,428 A | 6/2000 | Franks et al. |
| 6,127,155 A * | 10/2000 | Gelfand et al. ............... 435/188 |
| 6,153,412 A | 11/2000 | Park et al. |
| 6,294,365 B1 | 9/2001 | De Rosier et al. |
| 7,544,506 B2 | 6/2009 | Breidford et al. |
| 7,763,453 B2 | 7/2010 | Clemmens et al. |
| 2002/0173016 A1 | 11/2002 | Wurst et al. |
| 2003/0119042 A1* | 6/2003 | Franco De Sarabia Rosado et al. .................................. 435/6 |
| 2003/0152994 A1 | 8/2003 | Woudenberg et al. |
| 2004/0045827 A1* | 3/2004 | Mehta ........................... 204/450 |
| 2004/0241042 A1 | 12/2004 | Pugia et al. |
| 2005/0142563 A1 | 6/2005 | Haddad et al. |
| 2005/0142571 A1* | 6/2005 | Parthasarathy et al. ........... 435/6 |
| 2007/0003444 A1 | 1/2007 | Howell et al. |
| 2008/0064071 A1 | 3/2008 | Hogrefe et al. |
| 2009/0148933 A1 | 6/2009 | Battrell et al. |

FOREIGN PATENT DOCUMENTS

| | | |
|---|---|---|
| WO | 91/18091 A1 | 11/1991 |
| WO | 96/33744 A2 | 10/1996 |
| WO | 2005/118849 A1 | 12/2005 |
| WO | 2006/042838 A1 | 4/2006 |
| WO | 2007/106579 A2 | 9/2007 |
| WO | 2007/137291 A1 | 11/2007 |
| WO | 2008/036544 A1 | 3/2008 |
| WO | 2008/147382 A1 | 12/2008 |
| WO | 2008/155524 A1 | 12/2008 |

OTHER PUBLICATIONS

NP40 surfactant chemical structure (last viewed on Jan. 7, 2013).*
Colaço et al., "Extraordinary stability of enzymes dried in trehalose: simplified molecular biology," *Bio/Technology* 10:1007-11, Sep. 1992.
Crowe et al., "Preservation of Membranes in Anhydrobiotic Organisms: The Role of Trehalose," *Science* 223:701-3, 1984.
Crowe et al., "The role of vitrification in anhydrobiosis," *Ann. Rev. Physiol.* 60:73-103, 1998.
Dorfman et al., "Contamination-Free Continuous Flow Microfluidic Polymerase Chain Reaction for Quantitative and Clinical Applications," *Anal. Chem.* 77(11):3700-4, Jun. 1, 2005.
Franks, "Long-Term Stabilization of Biologicals," *Bio/Technology* 12:253-6, Mar. 1994.
Gibbs et al., "Nature of the Glass Transition and the Glassy State," *J. Chemical Physics* 28(3):373-393, Mar. 1958.
Green et al., "Phase Relations and Vitrification in Saccharide-Water Solutions and the Trehalose Anomaly," *J. Phys. Chem.* 93(8):2880-2, 1989.
Kajiwara et al., "Crystalline and amorphous phases in the binary system water-raffinose," *J. Chem. Soc. Faraday Trans* 93(9):1779-83, 1997.
Lukhtanov et al., "Novel DNA probes with low background and high hybridization-triggered fluorescence," *Nucl. Acids Res.* 35(5):e30, Jan. 26, 2007.
Marenco et al., "Fluorescent-Based Genetic Analysis for a Microfluidics Device," *Defence R&D Canada Contract Report*, Contract Number: W7702-00-R849/001/EDM, Mar. 2004, 170 Pages.
Mollmann et al., "The Stablility of Insulin in Solid Formulations Containing Melezitose and Starch," *Drug Dev. Indust. Pharmacy* 32:765-78, 2006.
Ramachandran et al., "Dry-reagent storage for disposable lab-on-a-card diagnosis of enteric pathogens," *Proceedings of the 1st Distributed Diagnosis and Home Healthcare (D2H2) Conference*, Arlington, Virginia, Apr. 2-4, 2006, 4 pages.
Ramanujam et al., "Ambient-Temperature-Stable Molecular Biology Reagents," *BioTechniques* 14(3):470-474, 1993.
Schebor et al., "Glassy State and Thermal Inactivation of Invertase and Lactase in Dried Amorphous Matrices," *Biotechnol Prog.* 13(6):857-63, 1997.
Slade et al., "Non-equilibrium behavior of small carbohydrate-water systems," *Pure & Appl. Chem.* 60(12):1841-64, 1988.
Wikipedia, "Injection molding"[Online] Oct. 17, 2007, XP002602263, URL=http://web.archive.org/web/20071019005409/http://en.wikipedia.org/wiki/Injection_molding> [retrieved on Sep. 23, 2010], p. 3, paragraph 3.
Wolanczyk, "Differential Scanning Calorimetry Analysis of Glass Transitions," *Cryo-Letters* 10:73-76, 1989.
Zhang et al., "Miniaturized PCR chips for nucleic acid amplification and analysis: latest advances and future trends," *Nucl. Acids Res.* 35(13):4223-37, Jun. 18, 2007.
Zhang et al., "Development of Continuous_flow PCR Chip Corresponding Technologies," *Journal of Instrumental Analysis* 23(6):114-118, 2004. (translation of abstract only).

* cited by examiner

REHYDRATABLE MATRICES FOR DRY STORAGE OF TAQ POLYMERASE IN A MICROFLUIDIC DEVICE

CROSS-REFERENCE TO RELATED APPLICATION

This application is a continuation of International PCT Patent Application No. PCT/US2010/038140, which was filed on Jun. 10, 2010, now pending, which claims the benefit under 35 U.S.C. §119(e) of U.S. Provisional Patent Application No. 61/186,441, filed Jun. 12, 2009, which applications are incorporated herein by reference in their entireties.

BACKGROUND

1. Field

The invention relates generally to the field of molecular diagnostic assays in microfluidic cartridges having on-board TAQ polymerase for PCR, where the TAQ polymerase is stabilized by dehydration without lyophilization.

2. Description of the Related Art

Dehydration is known to preserve the function of enzymes during storage above freezing, but the art is highly unpredictable, and methods and compositions must be varied for each enzyme studied—with no particular expectation of success. The DNA polymerases of thermophilic organisms used in PCR, generically referred to as "TAQ polymerases" by virtue of their first discovery in *Thermus aquaticus*, have proven particularly difficult in this regard. Nonetheless, the development of PCR products with a commercially useful shelf life at room temperature in a microfluidic device depends on a solution to this problem.

TAQ has 5'-3' polymerase and exonuclease activity, but not the 3'-5' proofreading capacity of other polymerases. The enzyme structure, however, is shared with other DNA polymerases and contains an opposable thumb-palm domain split by a deep cleft associated with DNA template binding. Features associated with thermostability include increased ratios of Arg to Lys, Glu to Asp, Ala to Gly, Thr to Ser, and an absence of cysteine. Folding at elevated temperature is maintained by hydrophobic, hydrogen bonding, electrostatic and van der Waal's interactions.

Enzymes are complex folded nanomachines, having cooperative motions and flexibility related to their catalytic function and folding. Certain structural sub-domains are relatively fixed in structure and others are more fluid and dynamic. Ideally, the native state is preserved during storage by dehydration, but dehydration most commonly results in some level of destabilization of folding. Denaturation and loss of activity results from enzyme unfolding; changes in structure following dehydration (or freezing) can be so severe that refolding into an active "native state" form does not occur following rehydration.

The role of water in enzyme structure is firmly established. The degree of hydration of a protein may be expressed by "Dh", where $Dh \cong 0.4$ (g $H_2O$/g protein) indicates a full hydration shell or monolayer of water surrounding the protein. Intermediate levels of hydration are also known. At $Dh \cong 0.15$-$0.2$ water is sufficient only to associate with more polar and ionic surfaces and enzymatic activity is lost. Most lyophilization processes result in $Dh \cong 0.02$. In the absence of the dielectric shielding of water, electrostatic interactions can result in denaturation. Water dominates protein structure by continuously breaking and reforming hydrogen bonds in the hydration shell (leading to both hydrophobic and hydrophilic interactions), as well as by guiding secondary and tertiary structure such as α-helix and β-turn motifs through interpeptide and side chain interactions. The liquid crystalline, hydrogen bonding capacity of water as a solvent lubricates or "plasticizes" the motions of structural domains of the enzyme.

Amorphous solids are preferred for "dry" storage of reagents because rehydration proceeds more rapidly than for the corresponding crystalline state. Ideally, the protein is stabilized in a solid, non-hygroscopic, glassy matrix, which undergoes a controlled devitrification when rehydrated with excess water. The preferred state has much in common with the glassy state formed by supercooling a liquid. Similarly, protein domains can be frozen in an amorphous "glassy" or gel-like state at or below a temperature $T_d$ (dynamical transition temperature), which is analogous to the $T_g$ (glass transition temperature) for formation of a glassy state in small molecules and polymers. Below $T_d$, protein unfolding is effectively inhibited. Similarly, dehydration to a critical level can be associated with inhibition of protein unfolding: at $Dh<0.2$ the hydration shell is patchy, and there are insufficient water molecules to execute the hydrogen bond rearrangements associated with unfolding of protein domains, even though the thermal energy available at room temperature is sufficient to denature the protein.

Of particular interest is the dehydration of proteins within glasses composed of lyoprotectants, molecules that protect the protein from denaturation during dry storage. Activity of lyoprotectants is perhaps best explained by a "water replacement model" in which the lyoprotectant is thought to interact directly with the protein through hydrogen and hydrophobic bonding, somehow offsetting the denaturing effect of removal of water. Glycerol, for example is thought to substitute for water in the protein's hydration shell and to effectively plasticize the dehydrated protein in a rehydratable form, albeit without the conformational instability of water.

Thus a common framework may be used to consider the amorphous glassy state formed by cooling a protein in an intimate mixture with a glass-forming molecule and the amorphous glassy state formed by dehydration of that mixture. The solid product in both cases is composed of protein conformers having varying degrees of native state which are "solvated" and molecularly dispersed in an amorphous glass such as a sugar. Protein and sugar mixtures for example have been found calorimetrically to have a bulk $T_g$ intermediate between the $T_g$ of the sugar and the $T_d$ of the protein in proportion to the composition of the mixture. Similarly, the $T_d$ of a protein may be modulated by intimate association of the protein with a suitable lyoprotectant, although the mechanism is not fully understood. Thus the conformation of the dewatered protein is believed to be somehow coupled to the molecular structure of the glass.

Candidate lyoprotectants include polyhydroxy compounds (PHCs) generally, particularly a variety of sugars (including monosaccharides, disaccharides, trisaccharides, and oligosaccharides), sugar alcohols, and a variety of polyhydoxy small molecules and polymers. Lactitol, mannitol, maltitol, xylitol, erythritol, myoinositol, threitol, sorbitol (glucitol), and glycerol are examples of sugar alcohols. Non-reducing sugars include sucrose, trehalose, sorbose, stachyose, gentianose, melezitose and raffinose. Derivatives of sugars that are lyoprotectants include methylglucoside and 2'-deoxyglucose, among others. Sugar acids include L-gluconate and metallic salts thereof. Less preferred for most applications include reducing sugars such as fructose, apiose, mannose, maltose, isomaltulose, lactose, lactulose, arabinose, xylose, lyxose, digitoxose, fucose, quercitol, allose, altrose, primeverose, ribose, rhamnose, galactose, glyceraldehyde, allose, apiose, altrose, tagatose, turanose, sophorose, maltotriose, manninotriose, rutinose, scillabiose, cellobiose, gentiobiose, and glucose. Also useful are polyvinylpyrrolidones, polyacrylamide, polyethylimine, pectin, cellulose, derivatized celluloses such as hydroxymethylcellulose, hydroxyethylcellulose, and hydroxypropylmethylcellulose, hydroxyethylstarch, soluble starches, dextrans, highly branched, high-mass, hydrophilic polysaccharides such as Ficoll®. Glass-forming albumins, gelatins and amino acids have also found use. By trial and error, useful mixtures of the above have also been discovered, typically differing for each target protein.

Success in formation of a glass is also known to be sensitive to rate of cooling, concentration, pressure and other process parameters such as the presence or absence of seed crystals. It must be recalled that a glass is a metastable state. The difficulties of these complex systems are illustrated by the following example, taken from WO 1996/033744, where it was reported that an amorphous solid freeze-dried composition of calcitonin 2% in lactose 95% with 2% residual water was raised above its $T_g$ of 40° C., resulting in irruptive crystallization of the lactose and formation of a water of crystallization composed of 60% water and 40% protein, which was excluded from the crystalline phase. The glass temperature of the solution phase was below freezing and as a result the protein then very rapidly lost biological activity at room temperature. Similar inactivation of enzymes has been noted with crystallized sucrose (Schebor C et al, 2008, Glassy state and thermal inactivation of invertase and lactase in dried amorphous matrices. Biotech Progress 13:857-863).

Rosen, as disclosed in expired U.S. Pat. No. 4,891,319, discovered that trehalose, which has a higher $T_g$ than lactose or sucrose, is lyoprotective when proteins are dried at room temperature, avoiding the rigorous conditions of freeze drying and spray drying, and reported that fluorescence markers may also be dehydrated in this way. Rosen suggested sugar:protein ratios of 1.4:1 to 10:1. Trehalose was proposed to act as a dry scaffold maintaining the structural integrity of the macromolecule when water was removed. These findings were further extending elsewhere (Colaco C et al, 1992, Extraordinary stability of enzymes dried in trehalose: simplified molecular biology, Bio/Technology 10:1007-11) and in U.S. Pat. No. 5,955,448 it was reported that various carbohydrates, including lactose or sucrose, may be employed as long as the formulation also includes an inhibitor of the Maillard browning reaction. Related observations have been reported by Franks (U.S. Pat. No. 5,098,893) and by Wettlaufer (U.S. Pat. No. 5,200,399), with comments on the importance of oxygen, light and chemical reactions in loss of activity of vitrified biological substances.

Sucrose, sorbitol, melezitose and raffinose have also been suggested as preferred lyoprotectants. However, to our knowledge, no success has been reported in stabilizing, without lyophilization, dry TAQ for extended storage stability periods with trehalose or any other sugar. To the contrary, in the declaration of A Madejón (FIG. 1—source: file wrapper of U.S. patent application Ser. No. 10/292,848), it is shown that trehalose is at most partially protective in dry reagent forms stored at 4° C. for 1 week, and is not as protective at 37° C. after one week as the standard PCR mixture without a lyoprotectant. Madejón further shows that melezitose of itself is not protective at all. Referring to the gel, lanes 1-9 (between the ladders) were run after reactant storage at 4° C.; lanes 10-18 after storage at 37° C. ("M"-melezitose, "L"-lysine, "G"-glycogen, "T"-trehalose, "S"-standard mix with no lyoprotectant).

Trehalose has been reported as unusual in that addition of small amounts of water does not depress $T_g$, as in other sugars (Crowe J H et al, 1998, The role of vitrification in anhydrobiosis. Ann Rev Physiol 60:73-103). Instead, a dihydrate crystal of trehalose forms, thereby shielding the remaining glassy trehalose from effects of the added water. Franks, however, in U.S. Pat. No. 6,071,428 shows that this effect is not remarkable, and that raffinose pentahydrate is also useful in storing enzymes in a dry state. The crystalline pentahydrate is reported to coexist with a surrounding glassy state of anhydrous material. These saccharides are not generally associated with formation of waters of crystallization or irruptive crystallization which would favor denaturation.

Arieli, in WO 2007/137291, proposes stabilization of TAQ with stabilizing agents such as sucrose, trehalose, melezitose, sugar alcohols, and reducing sugars in combination with BSA by drying above freezing, typically by drying at 55° C. for 1-3 hrs. Figures of the application demonstrate activity of TAQ after overnight or short term storage. However, no indication is given as to the degree of hydration (Dh) achieved in the drying process, and as is already known, TAQ retains full activity overnight in aqueous solution at room temperature (FIG. 2—source: Marenco A et al, 2004, Fluorescent-based genetic analysis for a microfluidics device, Defence R&D Canada Contract W7702-00-R849/001/EDM Final Report), and presumably for longer periods as well. Thus it is unclear whether the dehydration and glassy state achieved was sufficient for long term storage over months or years. Rosado has argued that TAQ is best stabilized in a fully hydrated "gelified" form, however the data presented in US Pat. Appl. 2003/0119042 to Rosado suggests that only limited duration of stability was achieved, perhaps a few days or weeks.

Development of frozen commercial formulations of TAQ have been reported in U.S. Pat. No. 6,127,155, for example. However, frozen storage requires special equipment typically not available at point-of-care facilities where microfluidic cards find usage. Also of note, a number of investigators have reported success lyophilizing TAQ preparations. These include Walker (U.S. Pat. No. 5,565,318), Treml (U.S. Pat. No. 5,763,157), and Park et al. (U.S. Pat. Nos. 5,861,251 and 6,153,412). Park describes lyophilization of TAQ in the presence of glucose, sorbitol, sucrose or Ficoll®. Klatser P R et al describe a lyophilized PCR Mix using trehalose as cryoprotectant and Triton X-100. Klatser found TAQ activity of their lyophilized mixture when rehydrated at up to 1 year post preparation. Commercially available lyophilized beads or frozen matrix containing TAQ with excipients are also available (Ready-to-Go PCR beads, Amersham Biosciences; Sprint™ Advantage®, Clontech, Mt View Calif.). Once lyophilized, the products are hygroscopic and sensitive to humidity and must be immediately sealed. The products apparently must also be held on ice during the rehydration process with ultra-pure water and refrigerated subsequently prior to use, rendering their use in next-generation, reagents-on-board microfluidic devices difficult if not impossible.

In contrast, next-generation microfluidic devices are configured so that use of ice or pure water during rehydration of reagents is not possible. The device reagents are typically rehydrated by sample or by an eluate prepared from the sample, for example by the method of Boom (U.S. Pat. No. 5,234,809). Thus, there is still a need in the art for a method of achieving ambient stabilization of DNA polymerase in the context of a PCR reagent mix that does not involve lyophilization and retains sufficient reliability over time to enable sensitive diagnostic assays in a microfluidic card.

Thus the disclosures to date do not apparently enable a formulation suitable for stable dry storage of TAQ polymerase without lyophilization or freezing. As commercialization of microfluidic devices for diagnostic applications moves closer to fruition, a workable solution to this problem is more urgently needed.

BRIEF SUMMARY

Room temperature dry storage of TAQ polymerase on microfluidic cards has proven difficult. Reagents are typically printed in the microfluidic channels of the card and then dried in place without freezing or lyophilization, which could disrupt the fabrication of the card device. We reasoned that an enzyme adapted for activity in a high temperature environment is likely to have a high $T_d$, as evidenced by a $V_{max}$ for many TAQ polymerases around 75° C., and to best preserve that native state, should be coupled in the vitrified state with a glass having a relatively high $T_g$. We also recognized that other excipients such as surfactants may be needed to stabilize the highly folded structure of TAQ during dry storage, particularly in microfluidic devices, because the reagent material is preferably printed on a low surface activity surface such as polyethylene terephthalate (PET) and is subjected to interfacial adsorption and denaturation during drying and rehydration. Once reagents are printed in place, the microfluidic devices are then further processed by lamination or ultrasonic welding, making lyophilization difficult or impossible.

Following a period of drying at controlled room temperature, the method relies on the use of a gel dessicant in sealed moisture-proof bags to complete the vitrification of the enzyme. The enzyme thus passes through a partially hydrated state over a period of a few weeks during dehydration. While not bound by theory, we believe that an extended progressive time-dehydration curve is essential for the enzyme to stabilize in native state during the gradual substitution of a sugar or polyol for water as hydrogen-bond donor. Surprisingly, we find that TAQ activity actually increases sharply during this drying process, taking for comparison the initial activity of a wet stock TAQ mixture during this period. While not bound by any particular theory, we explain this as recovery of latent activity of conformers in the frozen stock through a process of refolding in the partially hydrated state, which more closely resembles an intracellular cytosol in osmolarity. The material progresses from a gel to a composite gel-like glass during this process, developing a $T_g$ that is in excess of room temperature by virtue of the high $T_g$ of melezitose, a preferred lyoprotectant sugar. It was found that high molecular weight polyethylene glycol (PEG), bovine serum albumin (BSA), and optionally selected fluorosurfactants assisted in this process. Unexpectedly, in work to date, melezitose has outperformed trehalose in this process.

The method for printing and stabilizing a TAQ polymerase for storage on a microfluidic device as a gel-like glass above the freezing temperature of water, without lyophilization, includes the steps of:

a) combining the TAQ polymerase with an aqueous solution which comprises a combination of from about 1.0 to 10% w/v of a trisaccharide or trisaccharide hydrate; optionally from about 0.001% to 0.1% w/v of a high molecular weight polyethylene glycol; optionally from about 0.001 to 0.3% of a fluorosurfactant; from about 0.1 to 10% of a carrier protein; and a compatible buffer, thereby forming printable TAQ solution;

b) depositing on a plastic surface of said microfluidic card a droplet of the printable TAQ solution containing a quantity of the TAQ polymerase effective in polymerizing a nucleic acid;

c) briefly drying the droplet at a controlled room temperature or about 20° C. degrees to form a gel spot on the surface; and d) then closing and sealing the gel spot on the surface in a gas tight pouch under a dry atmosphere with a dessicant, the dessicant further vitrifying the gel spots during storage.

Advantageously, lyophilization and frozen storage conditions are not required. While not limited thereto, the method finds use in manufacture of microfluidic devices and kits for diagnostic nucleic acid assays.

BRIEF DESCRIPTION OF THE DRAWINGS

The teachings of the invention can be better understood by considering the following detailed description in conjunction with the accompanying drawings and claims, in which:

DETAILED DESCRIPTION

Figure 1:
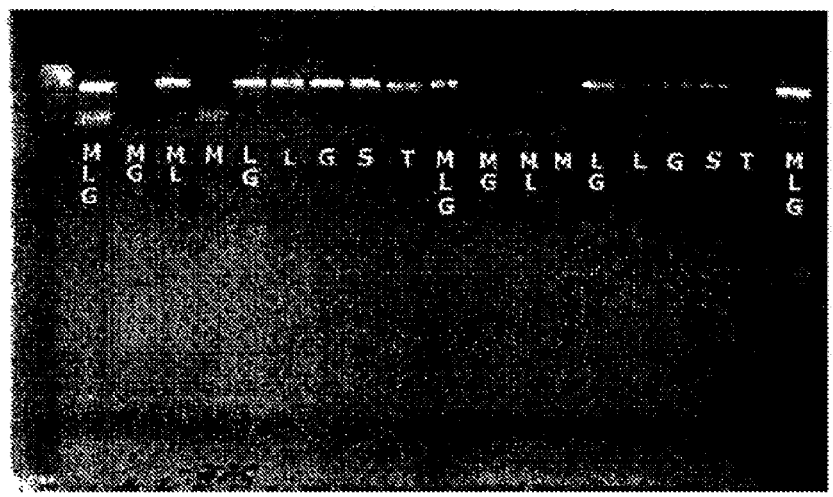
FIG. 1 is a reproduction of a gel demonstrating PCR amplification products in various dehydrated reaction mixtures. The figure is reproduced from the declaration of A Madejón (FIG. 1, top panel) of record in the file wrapper of U.S. patent application Ser. No. 10/292,848.
Figure 2:
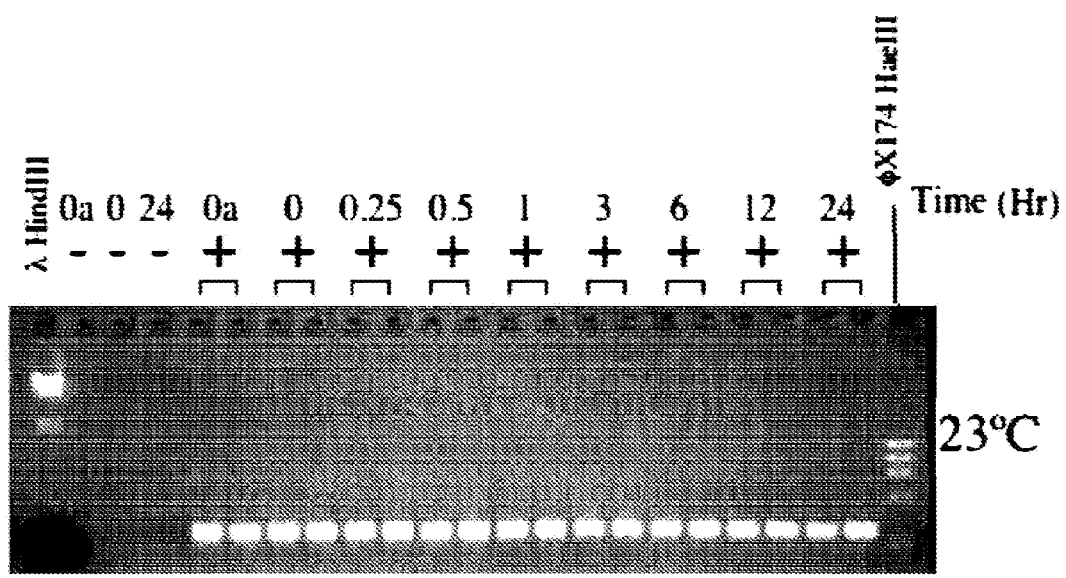
FIG. 2 is a reproduction of a gel demonstrating PCR amplification products following storage of TAQ reagent solutions overnight.

Certain meanings are defined here as intended by the inventors, ie. they are intrinsic meanings. Other words and phrases used here take their meaning as consistent with usage as would be apparent to one skilled in the relevant arts. When cited works are incorporated by reference, any meaning or definition of a word in the reference that conflicts with or narrows the meaning as used here shall be considered idiosyncratic to said reference and shall not supercede the meaning of the word as used in the disclosure herein.

DEFINITIONS

Lyoprotectant: a molecule that protects a protein, probe or primary, for example a TAQ polymerase, from denaturation and loss of biological activity during dry storage. Many lyoprotectants are polyols, but the class may also include amino acids, peptides, proteins, as well as PHCs, sugars, polyvinylpyrrolidinones, PEGs, and the like. It should be understood that the definition also includes co-lyoprotectants, where a first substance and a second substance having a synergic protective effect with the first are used in a mixture.

"$T_g$" is a glass transition temperature, the temperature above which the viscosity of an amorphous glassy material drops rapidly, progressing from a gel to a deformable plastic to a liquid, and conversely the temperature below which an amorphous non-crystalline solid forms. It has been thought that a $T_g$ of 40° C. or greater will ensure stability of a reagent at room temperature but this is unknown for TAQ polymerases. Generally $T_g$ is determined using differential scanning calorimetry (DSC) and can be defined as the onset, midpoint or endpoint of the transition. Technical details are provided in "Differential Scanning Calorimetry Analysis of Glass Transitions" by Jan P. Wolanczyk, 1989, Cryo-Letters, 10, 73-76 (1989) and Gibbs J H and E A DiMarzio, 1958, Nature of the Glass Transition and the Glassy State, J Chemical Physics 28:373-393. Glasses of value in the method are generally not formed from a pure glass precursor, but are instead formed from a lyoprotectant and a co-lyoprotectant, co-solvent, co-surfactant or added excipient as a mixture, and are thus termed "composite glasses". These composite glasses may have intermediate glass and "gel-like" properties and have hydration values ranging from about $0.01 \leq Dh \leq 0.4$, more preferably $0.022 \leq Dh \leq 0.2$. The $T_g$ of composite materials is generally dependent on the $T_g$ values of the individual constituents (Franks, F, 1994, Long term stabilization of biologicals, Bio/Technology 12:253-56). A preferred $T_g$ is greater than 20 degrees above the intended temperature of storage.

"Storage stability period" refers to a period of time, e.g. "shelf life", where a dry reagent mixture is stored in a microfluidic card under controlled conditions while retaining biological activity. A TAQ polymerase "retains its biological activity" in a reagent composition, if the biological activity of the biologically active material is efficacious at any given time in performing a PCR amplification. A preferred composition has a shelf life of greater than 6 months.

Probe: A "probe" is a nucleic acid capable of binding to a target nucleic acid by complementary base paring with sufficient complementarity to form a stable double 5 helix at room temperature. Probes may be labeled. Suitable labels that can be attached to probes include, but not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Fluorescent probes include intercalating probes, such as Cyber Green® (Molecular Probes), ethidium bromide, or thiazole orange, FRET probes, TaqMan® probes (Roche Molecular Systems), molecular beacon probes, Black Hole Quencher™ (Biosearch Technologies), MGB-Eclipse® probes (Nanogen), Scorpions™ (DxS Ltd) probes, LUX™ primer-probes (Invitrogen), Sunrise™ probes (Oncor), MGB-Pleiades (Nanogen), and so forth. Probe technologies are reviewed by Lukhtanov E A et al, 2007, Novel DNA probes with low background and high hybridization-triggered fluorescence, Nucl Acids Res 35:e30.

"Primer": is a single-stranded polynucleotide or polynucleotide conjugated capable of acting as a point of initiation for template-directed DNA synthesis in the presence of a suitable polymerase and cofactors. Primers are generally at least seven nucleotides long and, more typically range from 10 to 30 nucleotides in length, or longer. The term "primer pair" refers to set of primers including a 5' "forward" or "upstream" primer that hybridizes with the complement of the 5' end of the DNA template to be amplified and a 3' "reverse" or "downstream" primer that hybridizes with the 3' end of the sequence to be amplified.

Engineering and Handling of Microfluidic Devices for PCR

PCR in a microfluidic device is challenging due to the high surface area to volume ratio typical of the devices. Reaction volumes of a few microliters of sample are typical, and channel and chamber dimensions are typically smaller than 500 micrometers in width and perhaps 10 to 20% of that in depth.

The preferred microfluidic devices are small chemical reactors, preferredly mass produced from a plastic, having miniature channels and chambers containing pre-printed assay reagents.

In a preferred embodiment, all reagents required for performing a diagnostic assay are pre-positioned within the device so that the device is a self-contained disposable apparatus for performing a nucleic acid diagnostic assay. Optionally, the device also contains on-board diluents, wash solutions, and a waste trap of volume sufficient to contain all liquid wastes generated in the assay.

Details of the design and features of microfluidic cards suitable for practice of the present invention are disclosed for example in U.S. patent application Ser. No. 12/207,627, "Integrated Nucleic Acid Assays"; Ser. No. 11/562,611 "Microfluidic Mixing and Analytical Apparatus"; Ser. No. 12/203,715 "System and Method for Diagnosis of Infectious Diseases"; and Ser. No. 10/862,826 "System and Method for Heating, Cooling and Heat Cycling on Microfluidic Device", all co-assigned to the Applicant. The arts are the subject of a recent review by Zhang (2007, Miniaturized PCR chips for nucleic acid amplification and analysis: latest advances and future trends. Nucl Acids Res 35:4223-37).

As known in the art, microfluidic PCR may be performed in four configurations of PCR thermocycling reactors: a) serpentine, b) circular, c) reciprocating, and d) single chamber with localized heating and cooling. Serpentine reactors contain extended channels looping back and forth between two or three temperature zones, circular reactors are single loops crossing two or three temperature zones, reciprocating reactors contain two or three chambers at different temperatures, each chamber interconnected for exchange of the reaction mixture, and single chamber-based contain the reaction mixture with provision for localized heating and cooling, such as by Peltier thermoelectronics. Serpentine, circular and reciprocating reactors all require a pump or pumps to circulate the reaction mixture through or between temperature zones. Architecture of the microfluidic devices is varied to reflect these configurations.

Assays may include end-point or kinetic (also termed "real time") detection. Where an indicator reagent such as a probe is used, it may be added during the amplification or after the amplification. Preferred are fluorescent, fluorescence quenching, and "up-converting" fluorescent probes as are known in the art.

In a preferred embodiment, a biological sample containing a nucleic acid is pipette into a port in a microfluidic card, which is then sealed for the remainder of the assay. A pneumatic controller is used to direct the sample and liquid reagents as required to complete the assay. In a first step, the nucleic acid of the sample is optionally extracted on a solid phase matrix and rehydrated in a PCR buffer before being contacted with a dried PCR reagent containing primers. A dry reagent containing TAQ polymerase is provided separately. Thermocycling is then performed on card and positive detection of amplicon is made by a variety of methods, including use of fluorescent probes that are supplied on the microfluidic device.

Because of the interfacial tension between water and plastics, surfactants and co-surfactants such as PEG or albumin are sometimes used to reduce adsorption of biologicals to the plastic surfaces of the microfluidic device. Surface active agents known of value in reducing adsorptive losses include Tween-20, Triton X-100, Nonidet P40, PEG-8000 and bovine serum albumin. These substances also are thought to reduce aggregation of TAQ polymerase and are frequently used to increase polymerase activity. In general, dNTPs, magnesium salt, potassium chloride, sodium chloride, buffers, probe species, optionally primers, and non-specific wetting agents or surfactants are optionally combined in a "master-mix" that is aliquoted and dried on-board the microfluidic device.

During manufacture of a microfluidic device with on-board reagents, solutions containing glasses, excipients, and biological reagents are typically printed in the channels or chambers of the microfluidic devices using a variety of automated droplet dispenser equipment. A cover layer or lid is then applied to the device and the device is sealed. After assembly and inspection, the completed microfluidic devices are inserted into foil bags. A dessicant is placed in the bag with each device. Examples of dessicants which may be useful include silica gel, bentonite, borax, Anhydrone®, magnesium perchlorate, barium oxide, activated alumina, anhydrous calcium chloride, anhydrous calcium sulfate, titanium silicate, anhydrous calcium oxide, and anhydrous magnesium oxide, magnesium sulfate, and Dryrite®, among others, with or without indicator. The bags are then sealed using a thermal press sealer and stored for a designated shelf life.

Detailed Description

In order amplify a target nucleic acid sequence months after manufacture of a microfluidic device with on-board with reagents, an efficacious level of TAQ activity must be preserved during storage. Conditions for room temperature storage may be modified to prevent fluctuations in humidity by packaging the devices in sealed foil-lined bags with dessicant. After spotting the TAQ reagent in a buffered mixture with a glass lyoprotectant precursor and excipients onto the devices, the devices are sealed in the bags before full drying is achieved. At this stage the spots are gel-like in consistency. Following sealing in the bag, vitrification continues by a transfer of bound water from the reagent spot to the dessicant. By selection of a compatible glass/excipient composition, this method yields storage stable TAQ assembled in a self-contained microfluidic device which requires only addition of sample to run an assay.

Following a study of several hundred combinations of sugars, excipients, surfactants and carrier protein, trehalose and melezitose were selected for further study. We reasoned that an enzyme adapted for activity in a high temperature environment is likely to have a high $T_d$, as evidenced by a $V_{max}$ for many TAQ polymerases around 75° C., and to best preserve that native state, should be coupled in the vitrified state with a glass having a relatively high $T_g$. We also recognized that other excipients such as surfactants may be needed to stabilize the highly folded structure of TAQ during dry storage and to prevent loss of activity due to interfacial denaturation.

Trehalose is a disaccharide composed of two glucose molecules bound by an α,α-1,1 linkage. Since the reducing end of the glucosyl residues are connected with each other, trehalose has no reducing power. Trehalose is widely distributed in nature and protects organisms against various stresses, such as dryness, freezing, and osmopressure. Anhydrobiotic organisms such as brine shrimp and certain nematodes, which resist dessication, are able to tolerate the lack of water because of their high trehalose content; the trehalose playing a key role in stabilizing membranes and other macromolecular assemblies under extreme environmental conditions. Trehalose also has a higher glass transition temperature compared to other disaccharides and has a long history as a stabilizer in dessicated products (see for example Crowe J H et al, 1984, Preservation of membranes in anhydrobiotic organisms the role of trehalose, Science 223:701-703; U.S. Pat. Nos. 4,457,916, 4,206,200, and 4,762,857, and UK Patent GB 2 009 198), for which is believed to be superior to sucrose. Trehalose is widely believed to be superior to all other lyoprotectants (Colaco C et al. 1992. Extraordinary stability of enzymes dried in trehalose: simplified molecular biology. Bio/Technology 10:1007-11).

Melezitose (α-D-Glucopyranosyl-[1→3]-β-D-Fructofuranosyl-[2→1]-α-D-Glucopyranoside) hydrate is trisaccharide comprised of 2 glucose molecules and 1 fructose molecule with a molecular weight of 504.44 Da in the dry state. It is produced by many plant sap eating insects, including aphids and whiteflies. Melezitose is beneficial to the insects, as it reduces osmotic stress by reducing intracellular water potential as a storage carbohydrate. It is also widely known to function as a cryoprotectant and is used for frozen storage of a wide variety of mammalian cells because of its low osmolarity. Hydrolysis releases glucose and turanose, but the trisaccharide itself is non-reducing and is relatively resistant to Maillard browning. The glass transition temperature of melezitose is higher than that of disaccharides.

Comparative values for $T_g$ are shown in the following Table I:

TABLE I

|  | Tg (° K) | Tg (° C.) |
| --- | --- | --- |
| Glycerol | 180.0 | −93.2 |
| Sucrose | 348.0 | 74.9 |
| Raffinose (pentahydrate) | 352.7 | 79.6 |
| Raffinose (trihydrate) | 358.4 | 85.3 |
| Raffinose (anhydrous) | 376.4 | 103.3 |
| Trehalose (dehydrate) | 305.2 | 32.0 |
| Trehalose (anhydrous) | 352.2 | 79.0 |
| Stachyose (anhydrous) | 405.1 | 132.0 |
| Melezitose (anhydrous) | 433.1 | 160.0 |

The value for the $T_g$ of melezitose was obtained from "Mollmann, S H et al, 2006, The stability of insulin in solid formulations containing melezitose and starch. Drug Dev Indust Pharmacy 32:765-778. Other values were obtained from Green J L and C A Angell, 1989, Phase relations and vitrification in saccharide-water solutions and the trehalose anomaly, J Phys Chem 93:2880-82; Kajiwara K and F Franks, 1997, Crystalline and amorphous phases in the binary system water-raffinose, J Chem Soc Faraday Trans 93:1779-1783; Slade L and H Levine, 1988, Non-equilibrium behavior of small carbohydrate-water systems, Pure & Appl Chem 60:1841-64; and Heldman D R and D B Lund, 2006, Handbook of Food Engineering (2nd ed) CRC Press, Boca Raton Fla. Not all sources are in firm agreement; however it is generally agreed that $T_g$ increases with molecular weight and decreases with water of hydration.

Beginning with a hydrated sugar ensures that the $T_g$ is initially low and the formulation is a liquid, but upon dessication, $T_g$ will increase and will approach a value where room temperature storage is in the form of an amorphous glass. During this process, it is desirable that crystallization of anhydrous sugar not occur. Co-solvent excipients are useful to prevent undesirable crystallization and to more selectively associate with the TAQ polymerase, as is determined by a process of trial and error.

Formulation 1 consists of (as final concentrations in water) 1.5% melezitose hydrate, 0.005% Polyox™ WSR-301 (Amerchol Corp, Piscataway N.Y.), 0.1 mg/ml BSA and 10 Units TAQ polymerase in an aqueous solution. Following preparation of the TAQ solution stock with stabilizers, the clear gel precursor solution was applied in 3 uL spots to the internal surfaces of a plastic microfluidic device or card. Primers and probes were stored separately. The spots were allowed to dry for about 10 minutes or less at controlled room temperature and the plastic devices were then sealed in airtight pouches with dessicant sachets and stored at controlled room temperature. Polyox WSR-301 is a long-chain polyoxyethylene glycol (4 MDa molecular weight, also termed "PEG-90M"). Molecular biology grade water was used for all formulations. While bovine serum albumin is a preferred protein carrier, fish gelatin may also be used in the method. Betaine or lysine may also be used.

The following formulations were prepared for side-by-side comparison in a two month stability study: Formulation 2 was compounded as 1.5% trehalose, 0.005% Polyox WSR-301, 0.1 mg/ml BSA and 10 Units TAQ polymerase. Formulation 3 contained 1.5% melezitose hydrate, 0.1% Ficoll® 400, 0.1 mg/ml BSA. Formulation 4 contained 1.5% trehalose, 0.1% Fluorosurfactant FC4430 (3M Corp), and 0.1 mg/ml BSA. Formulation 5 contained 1.5% trehalose, 0.1% PEG8000, and 0.1 mg/ml BSA. Formulation 6 contained 1.5% trehalose, 0.1% Cellulose Gum 7LF, and 0.1 mg/ml BSA. Formulation 7 contained 1.5% lactitol, 0.005% Polyox WSR-301, and 0.1 mg/ml BSA. TAQ used in these experiments was EconoTaq® Plus (Lucigen Corp, Middleton Wis.) formulated at 10 U/uL.

All formulations were mixed with a standard quantity of TAQ polymerase and spotted on a plastic surface for testing. Following spotting, the gel composite precursor spots were allowed to set briefly for about 10 minutes and then closed and sealed in a moisture-proof, gas-tight pouch along with an excess quantity of a dessicant. Typically, silica gel or bentonite with indicator is used. The pouches were thermally sealed under an inert, dry gas atmosphere.

Formulations may also include a glass-compatible PCR enhancer selected from betaine, n-formyl morpholine, δ-valerolactam (2-piperidone), ε-caprolactam, 1,2-cyclopentanediol, PVP-10, PVP-40, or a mixture thereof; and an excipient selected from inulin, cellulose, derivatized cellulose, polyvinylpyrrolidone, lysine, arginine, or a Maillard reaction inhibitor. Enhancers serve multiple functions, including improving performance of GC-rich DNA substrates as templates and increasing specificity and yield. Various amides, sulfoxides, sulfones, and diols are known to improve PCR yield and specificity, often dramatically better than betaine. DMSO, tetramethylene sulfoxide, formamide, 2-pyrrolidone are examples. Some enhancers, such as n,n-dimethyformamide and DMSO have been used to reduce the temperatures required for thermocycling, which in saline may require heating the solution to near-boiling, with attendant issues of pressure and outgassing. However, enhancers that can be stored in dry form as a composite as a gel or glass are required here.

Enhancers include glass formers of value as co-lyoprotectants. These enhancers include n-formyl morpholine (melting point 23° C.), δ-valerolactam (2-piperidone, melting point 38-40° C.), ε-caprolactam (melting point 69-70° C.), and 1,2-cyclopentanediol (melting point of 54-56° C.). PVP-10 is reported to have a glass transition temperature of 66° C. and PVP-40 a $T_g$ of 99° C. Other glass formers of function in improving PCR include amino acids such as lysine, low molecular weight amides, carbohydrates such as glycogen and inulin, albumins (both HSA and BSA), and a range of sugars as earlier discussed.

Figure 3:
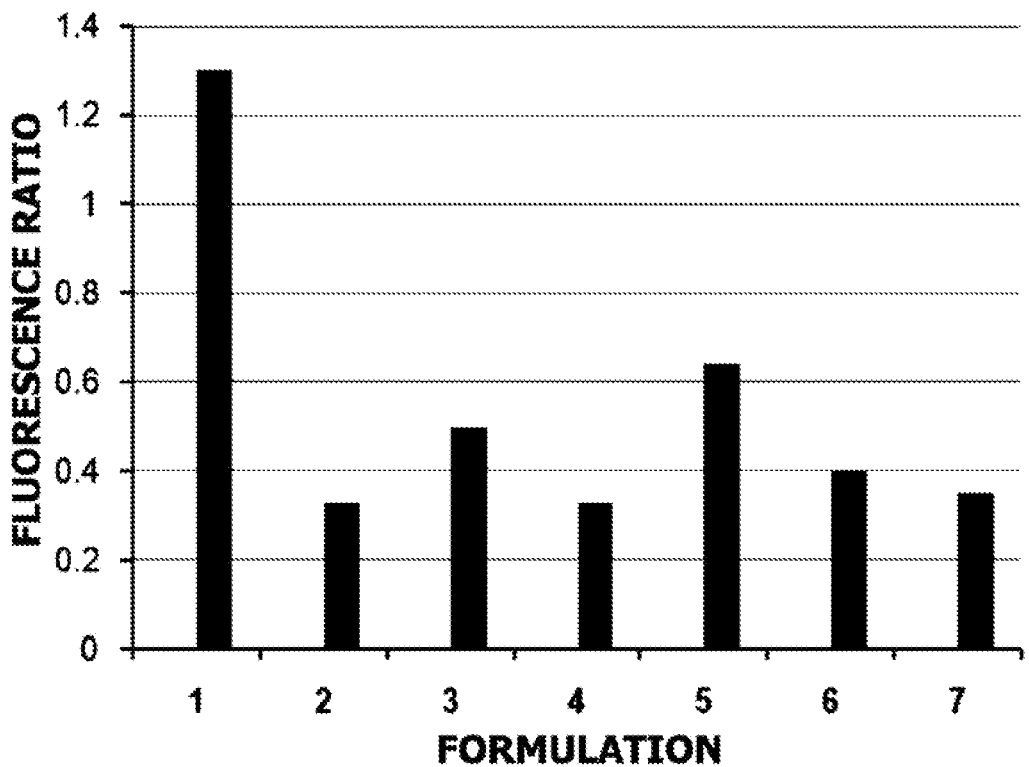
FIG. 3 is a bar graph comparing formulations of TAQ following dry storage for two months.

The data at 2 months stability storage testing are reported in FIG. 3. The results are shown as fluorescence ratio normalized for activity of a freshly mixed "wet" amplification performed without drying. As can be seen, most formulations failed to maintain full potency. However, Formulation 1, the melezitose/Polyox WSR-301/BSA based formulation is seen to outperform the standard wet amplification mixture by a factor of 1.3 after 2 months storage at room temperature. In contrast, melezitose hydrate prepared with Ficoll 400 was not convincingly stable after two months, and trehalose formulated with Polyox WSR-301 or a variety of alternate excipients similarly failed to provide a suitable storage stability period.

Figure 4:
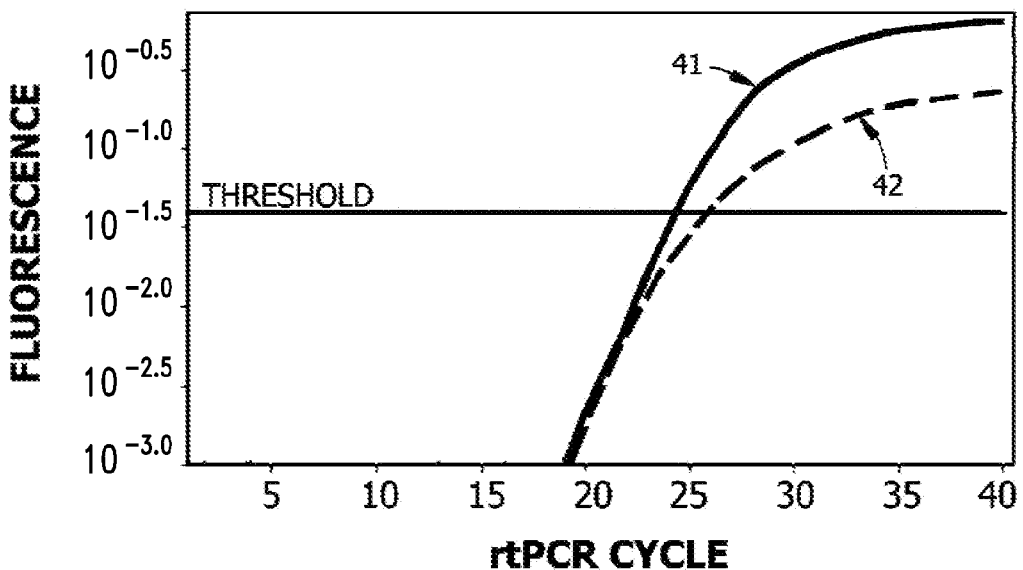
FIG. 4 is a rtPCR curve showing TAQ activity of a dry mixture following rehydration versus a freshly prepared wet reaction mixture (undried).

In these studies, a *Salmonella paratyphi* primer pair having 5000 copies/reaction was used for amplification. The rehydrated complete amplification mixtures were thermocycled and detection completed using a molecular beacon or FRET probe. Ct and fluorescence yield ratio were measured for each reaction. A sample real time PCR amplification curve, comparing melezitose Formulation 1 after extended dry storage and a fresh wet reaction is shown in FIG. 4. The solid curve (41) is the activity of the dried TAQ reagent, the dotted line curve (42) is the activity of the standard wet TAQ reaction mixture.

Figure 5:
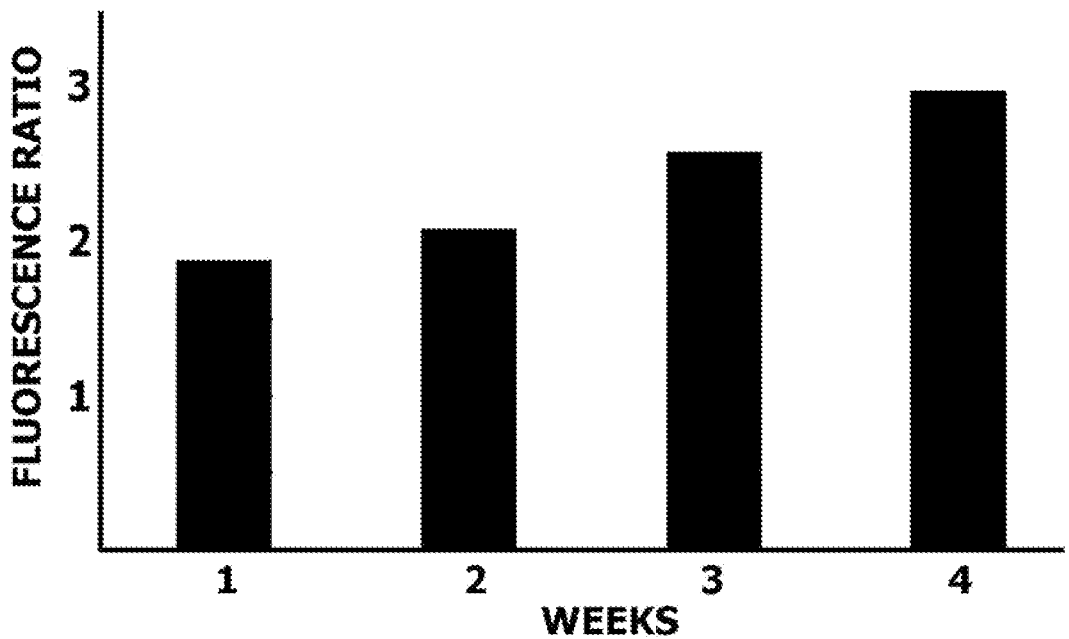
FIG. 5 is a bar graph showing increase in TAQ potency over commercially supplied stock during progressive vitrification in a melezitose glass at room temperature.

In FIG. 5, the behavior of the melezitose of Formulation 1 as a function of storage stability period is examined further. It can be seen that during the initial period of processing, TAQ polymerase activity steadily increases over a 4 week period. The fluorescence ratio again is the ratio of fluorescence achieved in real time PCR. We interpret this result as not artifactual; it may represent recruitment of native state conformers from a stock solution of TAQ molecules damaged during the manufacturing and storage process. While not bound by theory, it is thought that commercially available frozen preparations contain a percentage of freeze-denatured TAQ molecules, mixtures of conformers, some as native state conformation and some not, some variants less active than others, and the stabilization procedure has the effect of repairing the conformational state of at least some of these.

Figure 6:
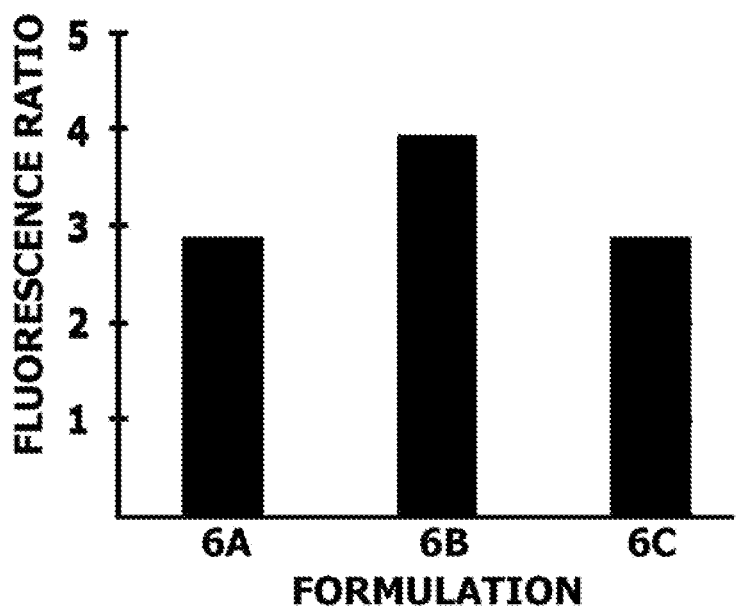
FIG. 6 is a bar graph showing TAQ potency following vitreous storage in melezitose versus trehalose with selected excipients.

FIG. 6 compares three formulations in amplifications with a different primer system. Formulations 6A, 6B and 6C are compared, where 6A is equivalent to Formulation 3 above, 6B is equivalent to Formulation 1 above, and 6C is equivalent to Formulation 5 above. As can be seen, the formulation containing melezitose 1.5%/0.005% Polyox WSR301/0.1 mg/ml BSA is again superior after dry storage by the method of sealing gel spots in gas-tight pouches with desicant so that a gradual, progressive dewatering of the enzyme is achieved.

Figure 7:
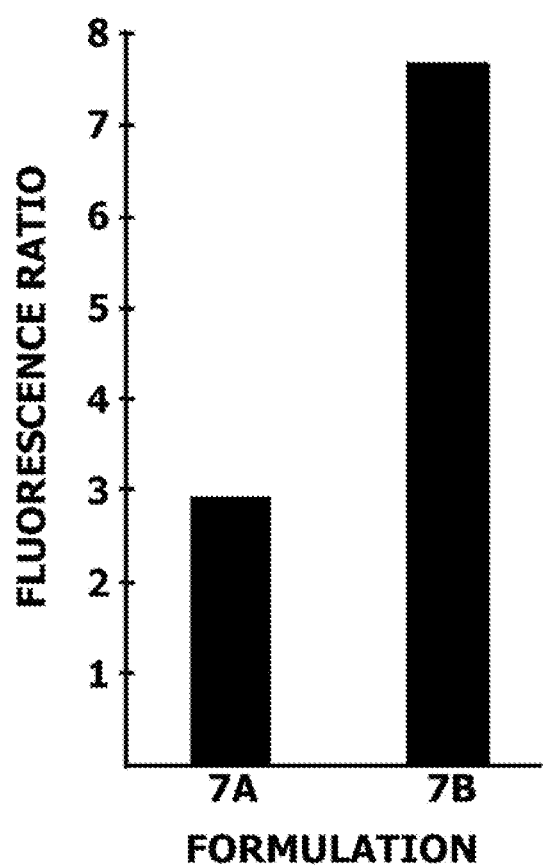
FIG. 7 shows TAQ potency following vitreous storage with excipient fluorosurfactant FC-4430 (3M Corp).

FIG. 7 compares a Formulation 7A containing trehalose with 0.1% PEG8000 with a Formulation 7B containing trehalose with 0.1% Fluorosurfactant FC4430. Surprisingly, the fluorosurfactant had a remarkable effect on fluorescence yield in this 2 week dry storage data.

FIGS. 6 and 7 involve asymmetric amplification of a malaria primer system where the forward and reverse primers are presented in a 10:1 ratio, using 5000 copies/reaction of the forward primer. In all instances, a reaction was run in parallel using fresh frozen reagents.

EXAMPLES

Example 1

PCR Standard Reaction

As a wet standard reaction, stock frozen TAQ polymerase was added to freshly prepared PCR reagent stock mix according to the following Table II.

TABLE II

| COMPOSITION | Stock Concentration | Volume of Reaction (uL) | Final Concentration |
|---|---|---|---|
| 100 mM Tris pH 8.0, 500 mM KCl, 15 mM MgCl$_2$ | 10x | 2.0 | 1x |
| MgCl$_2$ | 50 mM | 1.4 | 3.5 mM |

TABLE II-continued

| COMPOSITION | Stock Concentration | Volume of Reaction (uL) | Final Concentration |
|---|---|---|---|
| dNTPs | 10 mM | 0.4 | 0.2 mM |
| Primer/Probe Mix | 20x | 1.0 | 1x |
| TAQ polymerase | 2.5 U/uL | 0.4 | 1 U |
| Std DNA template |  | 5.0 |  |
| water |  | 9.8 |  |
| Total Volume |  | 20.0 uL |  |

The reaction mixture was thermocycled using a Rotor Gene® Q (Qiagen Carlsbad Calif.) thermocycler with rtPCR monitoring. Real time PCR was monitored to obtain crossing threshold (Ct); i.e., the measurement the cycle number at which the increase in fluorescence (and therefore DNA) is exponential and the fluorescence yield ($F_{STD}$). A melt curve was run on all successful amplifications to verify correct amplification of the target amplicon. Endpoint detection may also be used. Optionally, a FRET melting curve may be included to verify the identity of the amplicon.

Example 2

Dry Reagent Assay

Reaction mixes containing TAQ polymerase, lyoprotectant, co-lyoprotectant, and protein carrier or excipient, as well as KCl, $Mg^{2+}$, and dNTPs, where prepared as about a 5× stock and spotted in a microfluidic card or on a plastic surface as 3 uL spots. The spots were allowed to gel at room temperature for about 10 min or less, and then placed in foil bags supplied by Vaporflex Preservation Packaging (LPS Industries, Moonachie, N.J.). To reconstitute, a volume of 15 uL containing target DNA and primers was used.

The reconstituted volume was then amplified in the presence of primers and template in a Rotor Gene®. Ct and fluorescence yield ($F_X$) were measured and compared to the standard, wet mix (above). A fluorescence ratio was calculated ($F_X/F_{STD}$).

Melezitose, trehalose, lactulose and other sugars were obtained from Sigma Chemicals (St Louis Mo.). Polyol WRS301 (also known as "PEG 90M", 1% viscosity 1650-550 cps, 4 MDa MW) is supplied by Amerchol Corp, Piscataway N.Y. Fluorosurfactant FC-4430 was obtained from 3M Corp. Reagents were molecular biology grade where possible.

Example 3

Formulation 1

A formulation for ambient dry storage of TAQ polymerase in a microfluidic device was prepared per Table III. Sugar was added from a 25% solution of melezitose hydrate in water. A stock containing 0.01% Polyol WRS301 as excipient was used in this example.

TABLE III

| COMPOSITION | Stock Concentration | Volume per Reaction (uL) | Concentration per Reaction |
|---|---|---|---|
| 1M Tris pH 8.4, 2.5M KCl | 50x | 0.3 | 20 mM Tris, 50 mM KCl |
| dNTP Mix | 10 mM | 0.3 | 0.2 mM |
| $MgCl_2$ | 1M | 0.15 | 10 mM |
| BSA | 25 mg/ml | 0.15 | 0.25 mg/ml |
| Sugar | 25% | .9 | 1.50% |
| Excipient | varies | .15 | varies |
| TAQ polymerase | 10 U/uL | 0.96 | 10 U |
| Total volume on rehydration with target DNA/primer solution |  | 15 uL |  |

The resulting clear gel composite precursor solution was spotted with a pipet onto a passivated plastic surface (PET) of a microfluidic device. Spots were allowed to set for about 10 min and then sealed in foil bags with dessicant. A chromogenic indicator was used to verify the integrity of the sealed bags during storage. The pouches were heat sealed under a dry gas atmosphere before storage.

While the above is a complete description of the presently preferred embodiments of the present invention, it is possible to use various alternatives, modifications and equivalents. All of the US patents, US patent application publications, US patent applications, foreign patents, foreign patent applications and non-patent publications referred to in this specification, claimed as priority documents, and/or listed in any Information Data Sheets, are incorporated herein by reference, in their entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for stabilizing a TAQ polymerase for printing and storage in a microfluidic cartridge, the method comprising:
   a) combining said TAQ polymerase with an aqueous solution to form a printable solution, the aqueous solution comprising:
      i) from about 1.0% to 10% w/v of a trisaccharide;
      ii) optionally from about 0.001% to 0.1% w/v of a high molecular weight polyethylene glycol (PEG);
      iii) from about 0.001% to 0.3% w/v of a fluorinated surfactant;
      iv) from about 0.1 mg/ml to 10 mg/ml of a carrier protein; and
      v) a compatible buffer;
   b) depositing on a surface of the microfluidic cartridge a droplet of said printable solution containing a quantity of said TAQ polymerase effective in polymerizing a nucleic acid;
   c) drying said droplet at a controlled room temperature to form a gel spot on said surface; and
   d) closing and sealing said gel spot on said surface in a gas tight pouch under a dry atmosphere with a dessicant, said dessicant further vitrifying said gel spot during storage.

2. The method of claim 1, wherein said trisaccharide is melezitose or raffinose.

3. The method of claim 1, wherein said high molecular weight polyethylene glycol is PEG90M.

4. The method of claim 1, wherein said high molecular weight polyethylene glycol has a molecular weight of 1 to 5 MDa.

5. The method of claim 1, wherein said carrier protein is bovine serum albumin or fish gelatin.

6. The method of claim 1, wherein said fluorinated surfactant is a non-ionic fluoroalkylsurfactant.

7. The method of claim 6, wherein said fluorinated surfactant is Fluorosurfactant FC-4430.

8. The method of claim 1, wherein said aqueous solution further comprises a PCR enhancer selected from betaine, n-formyl morpholine, δ-valerolactam (2-piperidone), ε-caprolactam, 1,2-cyclopentanediol, polyvinylpyrrolidone, or a mixture thereof.

9. The method of claim 1, wherein said aqueous solution further comprises inulin, cellulose, derivatized cellulose, polyvinylpyrrolidone, lysine, arginine, or a Maillard reaction inhibitor.

10. The method of claim 1, wherein the controlled room temperature is about 20° C. degrees.

11. A method for stabilizing a TAQ polymerase for printing and storage on a microfluidic cartridge, without lyophilization, said method comprising:
   a) combining said TAQ polymerase with an aqueous solution to form a solution, said aqueous solution comprising:
      i) from about 1.0% to 10% w/v of a trisaccharide;
      ii) optionally from about 0.001% to 0.1% w/v of a high molecular weight polyethylene glycol (PEG);
      iii) from about 0.001% to 0.3% of a fluorinated surfactant;
      iv) from about 0.1 mg/ml to 10 mg/ml of a carrier protein; and
      v) a compatible buffer;
   b) depositing on a surface of the microfluidic cartridge a droplet of said printable TAQ solution comprising a quantity of said TAQ polymerase effective for polymerizing a nucleic acid;
   c) drying said droplet at a controlled room temperature to form a partially vitrified gel spot on said surface; and
   d) closing and sealing said gel spot on said surface in a gas tight pouch under a dry atmosphere with a dessicant, said dessicant further vitrifying said gel spot during storage.

12. The method of claim 11, wherein said trisaccharide is melezitose or raffinose.

13. The method of claim 11, wherein said high molecular weight polyethylene glycol is PEG90M.

14. The method of claim 11, wherein said high molecular weight polyethylene glycol has a molecular weight of 1 to 5 MDa.

15. The method of claim 11, wherein said carrier protein is bovine serum albumin or fish gelatin.

16. The method of claim 11, wherein said fluorinated surfactant is a non-ionic fluoroalkylsurfactant.

17. The method of claim 16, wherein said fluorinated surfactant is Fluorosurfactant FC-4430.

18. The method of claim 11, wherein said aqueous solution further comprises a PCR enhancer selected from betaine, n-formyl morpholine, δ-valerolactam (2-piperidone), ε-caprolactam, 1,2-cyclopentanediol, polyvinylpyrrolidone, or a mixture thereof.

19. The method of claim 11, wherein said aqueous solution further comprises inulin, cellulose, derivatized cellulose, polyvinylpyrrolidone, lysine, arginine, or a Maillard reaction inhibitor.

20. The method of claim 11, wherein the controlled room temperature is about 20° C. degrees.

* * * * *